US00PP11159P

United States Patent [19]

Hodell

[11] Patent Number: Plant 11,159

[45] Date of Patent: Dec. 21, 1999

[54] ANTHURIUM PLANT NAMED 'MISS MINI PURPLE'

[76] Inventor: Charles W. Hodell, P.O. Box 730, Waimanalo, Hi. 96795

[21] Appl. No.: 08/998,746

[22] Filed: Dec. 29, 1997

[51] Int. Cl.[6] ..... A01H 5/00

[52] U.S. Cl. ..... Plt./368

[58] Field of Search ..... Plt./368, 365

[56] References Cited

U.S. PATENT DOCUMENTS

P.P. 9,449 2/1996 Lamb ..... Plt./368

OTHER PUBLICATIONS

Kamemoto, Breeding Anthuriums in Hawaii, University of Hawaii Press, pp. 9–10, 1996.

*Primary Examiner*—Howard J. Locker
*Assistant Examiner*—Kent L. Bell

[57] ABSTRACT

A distinct new cultivar of Anthurium named 'Miss Mini Purple', characterized by its bright lilac-purple spathes held well above the foliage. The foliage mass is compact and symmetrical, with leathery dark green leaves with a soft sheen, sunken veins and midrib.

2 Drawing Sheets

BACKGROUND OF THE VARIETY

The present invention comprises a new and distinct cultivar of Anthurium, botanically known as an interspecific hybrid and referred to by the cultivar name 'Miss Mini Purple'.

The new cultivar is the product of a planned breeding program carried out by the inventor in Waimanalo, Hi. The cross was between an unnamed plant of *Anthurium amnicola* origin and an unnamed plant of *Anthurium antioquiense* origin. For the specific reference, see Kamemoto, *Breeding Anthuriums in Hawaii,* University of Hawaii Press 1996, pp. 9–10.

The new cultivar was discovered from the progeny of the stated cross and was originally designated L128D during testing, but was subsequently named 'Miss Mini Purple'. Asexual reproduction of the new cultivar by divisions in Waimanalo, Hi. have shown that the cultivar's unique characteristics remain stable from generation to generation.

The following observations were made under normal shade house conditions for Anthuriums grown in Waimanalo, Hi. The daytime temperature ranged from 22° C.–33° C. The nighttime temperatures ranged from 16° C.–26° C.

The following traits have been repeatedly observed to be characteristics which in combination distinguish the new cultivar from other cultivars known to the inventor, particularly plants of *Anthurium amnicola,* to which comparative references are made.

1. The instant cultivar produces an abundance of intense lilac-purple spathes, with dark maroon spadices. Once open, the spathes fade from purple to lavender over an 8–10 week period. By comparison, the spathes of plants of *A. amnicola* begin as lavender and fade to a dull white and last about half as long as that of 'Miss Mini Purple'.

2. Once opened, spathes remain upright throughout their life, while those of *A. amnicola* reflex in a week or two.

3. The spathes are held well above the leaf canopy.

4. The instant cultivar remains compact, symmetrical, and free branching. By comparison, plants of *A. amnicola* branch inconsistently, drop lower leaves and becomes uneven in growth habit, and are less than half the size of the instant cultivar when mature.

5. The leaves are long lasting, durable, and dark green with a soft reflective sheen. Plants of *A. amnicola* have leaves that are medium green, narrower and have a tendency to die back.

6. Venation on the leaf upper side is sunken and in a pattern that traces a leaf within a leaf. On the underside the veins are raised.

7. 'Miss Mini Purple' exhibits strong reistance to disease and pests.

8. The spathes give off a mild camphor-eucalyptus scent while receptive, which is sweeter than that given off by plants of *A. amnicola.*

'Miss Mini Purple' differs from plants of *A. antioquiense* by having larger ovate lilac-purple spathes and ovate foliage.

BRIEF DESCRIPTION OF THE DRAWINGS

The color photographic drawing in FIG. 1 shows a top perspective of the spathes and foliage of a plant of 'Miss Mini Purple' in a 6 inch pot approximately 52 weeks after planting an unrooted cutting, and grown under appropriate conditions.

The color photographic drawing in FIG. 2 shows a spathe enlarged approximately 2 times its natural dimensions. Colors are as accurate as possible with color illustrations of this type.

DETAILED DESCRIPTION OF THE VARIETY

Figure 1:
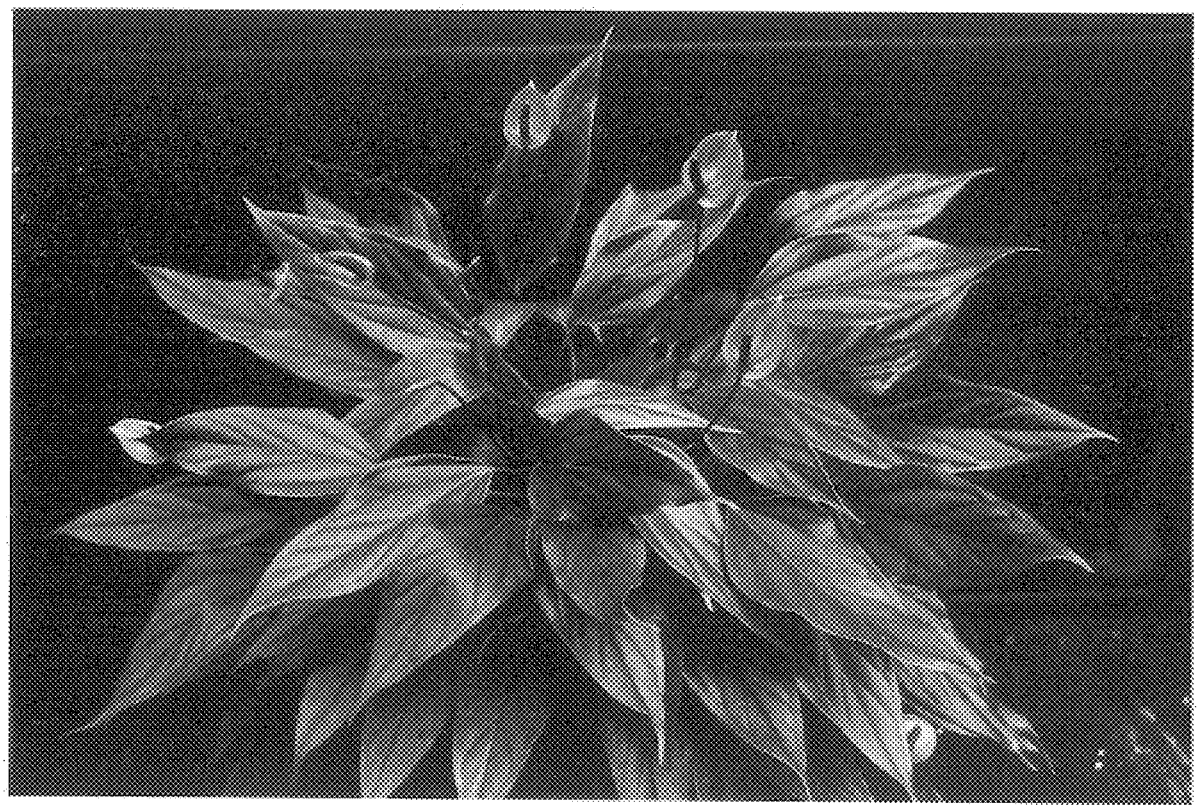
Figure 2:
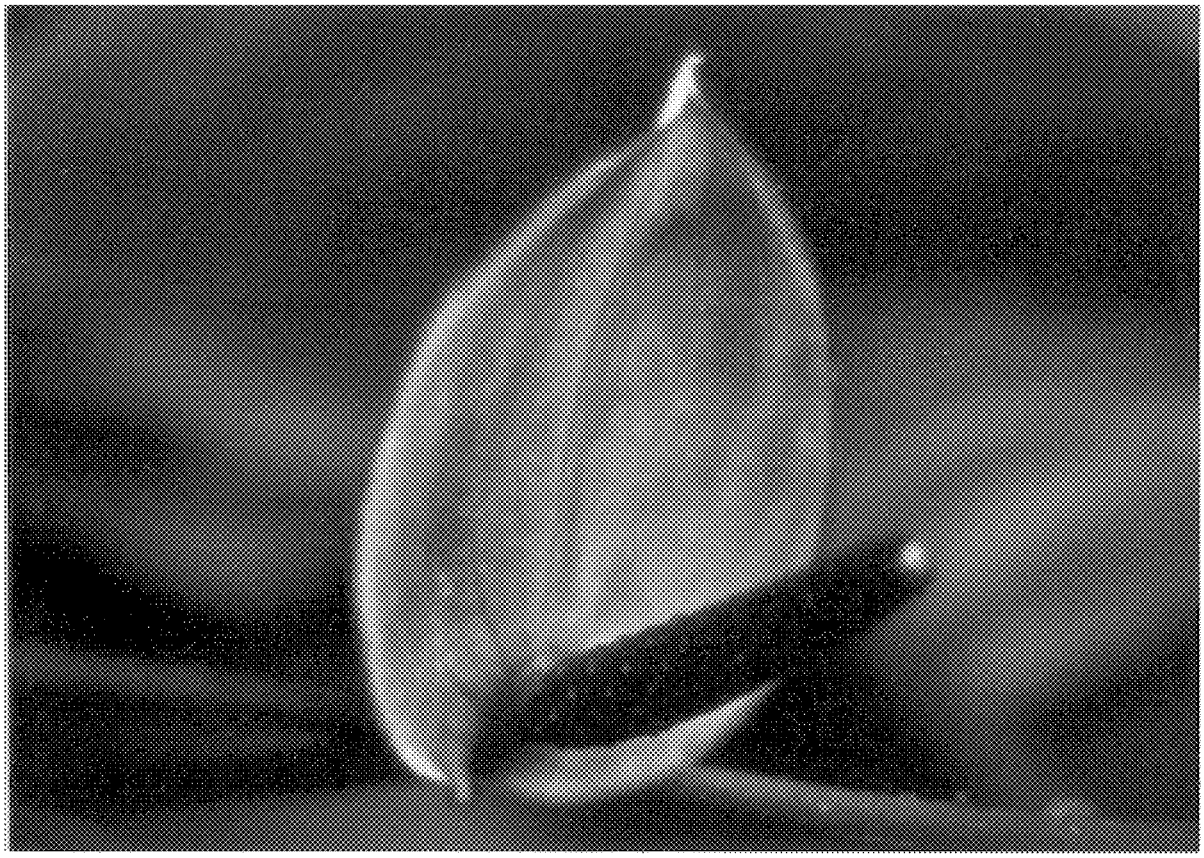

All color references are measured against the color charts in *The Color Dictionary* by Maerz and Paul. Colors are approximate as colors depend on light levels, temperature and fertilization, without varying the genotype.

Origin: Seedling from unnamed parents of the genus Anthurium.

Classification: Anthurium hybrid 'Miss Mini Purple'.

Propagation: Asexual production through division at Waimanalo, Hi.

Plant: In a 6" pot grown for a period of 52 weeks, the foliage canopy extends 30 cm above the soil line and has a diameter of 40 cm at its widest. It is full and symmetrical.

Leaves:

*Form.*—The leaf blade is ovate with an acuminate tip and an attenuate base. The margin is entire. Most leaves are moderately wavy their entire length. The leaf blades angle between 30°–90° from the line of the petiole. At the top of the canopy, the leaves are mostly horizontal to the ground, while at the sides they mostly point down.

*Size.*—The leaf blades are approximately 5.5 cm to 7 cm in width and 15 cm to 18 cm in length.

*Color.*—The mature leaf blade is closest in color to 24 H7 on upper surface. The lower surface is closest to 21 K2. Immature leaves have an upper surface closest to 14 J9 and a lower surface of 21 K2.

*Petioles.*—Petioles are approximately 11–14 cm long and 2.5 mm to 3 mm in diameter. The color of the outward facing side is close to 21 L7 and the inward facing side 21 L5.

*Geniculum.*—The geniculum is approximately 3 mm to 4 mm in diameter and 3 cm in length. The outward facing color is close to 15 L6 while the inward facing color is close to 15 L9.

*Venation.*—Venation on the leaf upper surface sunken, and raised on the leaf lower surface. The midrib is generally straight with a slight downturn at the tip of about 2 cm in length. The midrib coloration is 21 L7 on the upper surface and 21 L5 on the lower surface.

Spathe/spadix:

*Immature.*—The spathe is tightly rolled around the spadix as it extrudes from the petiole sheath. It is fully opened after 4–5 weeks. The peduncle reaches a length of 22 cm to 24 cm and is 2 mm to 3 mm in diameter. The color of the peduncle nearest the spathe is 47 L3. That color gradually changes to 46 K1 halfway down the peduncle and continues to the base.

*Mature.*—The mature spathe once opened is ovate with a cuspidate tip and an obtuse base. The dimensions are 3 cm to 5 cm wide and 4 cm to 6 cm long. The color of the upper surface is 42 L9 when first open. It gradually fades to 41 G7 after several months. The lower surface begins as 41 I7 and fades to 41 G7. The apex curves upward and is approximately 0.5 cm in length. Its color is from 26 B1 to 26 D1. The lastingness of the opened spathe is approximately 10–14 weeks. A plant grown from a single cutting in a six-inch pot will normally have between 8 to 10 spathes in various stages of maturity on 4 to 6 shoots after approximately 10 months. The dimensions of the spadix are 3 cm to 4 cm in length. The thickness at the base is 6–8 mm and at the tip 4–6 mm. The color is close to 47 L9 at the start, and only lightens slightly to 47 L7 over its life. The reproductive organs are typical of the two species and produce viable seed, but 'Miss Mini Purple' does not produce pollen. The female inflorescences (true botanical flowers) are inconspicuous and also give off a mild sweet scent while receptive.

It is claimed:

1. A new and distinct cultivar of Anthurium plant named 'Miss Mini Purple', as described and illustrated.

* * * * *